(12) United States Patent
Chiu et al.

(10) Patent No.: US 8,899,277 B2
(45) Date of Patent: Dec. 2, 2014

(54) MANUFACTURING METHOD OF MEDICAL TEXTILES WOVEN FROM CHITOSAN CONTAINING HIGH WET MODULUS RAYON FIBRE

(75) Inventors: Ming Houng Chiu, Taipei (TW); Ming Shuen Hong, Changhua County (TW); Chi Ming Chiu, Taipei (TW); Tang Chin Hung, Changhua County (TW)

(73) Assignee: Shin Era Technology Co., Ltd., Taipei ( * ) Notice: Subject to any disclaimer, the term of this patent is extended or adjusted under 35 U.S.C. 154(b) by 0 days.

(21) Appl. No.: 13/566,550

(22) Filed: Aug. 3, 2012

(65) Prior Publication Data

US 2014/0034181 A1 Feb. 6, 2014

(51) Int. Cl.
*C08B 37/08* (2006.01)
*D01F 1/10* (2006.01)
*D03D 15/00* (2006.01)
*D03D 25/00* (2006.01)

(52) U.S. Cl.
USPC ............ 139/426 R; 139/383 R; 139/420 R; 139/420 A; 139/420 B; 424/402; 424/445

(58) Field of Classification Search
USPC ...... 139/383 R, 420 R, 420 A, 426 R, 420 B; 264/176.1, 204, 205, 207, 210, 210.1, 264/210.2, 210.3, 211.12, 211.13, 211.15, 264/211.16, 211.18, 211.19, 211.2
See application file for complete search history.

(56) References Cited

U.S. PATENT DOCUMENTS

| | | | |
|---|---|---|---|
| 5,114,788 A * | 5/1992 | Nakagawa et al. | 442/77 |
| 5,603,884 A * | 2/1997 | DuCharme et al. | 264/203 |
| 5,622,666 A * | 4/1997 | Struszczyk et al. | 264/191 |
| 5,718,954 A * | 2/1998 | Sano et al. | 428/35.6 |
| 5,744,251 A * | 4/1998 | DuCharme et al. | 428/536 |
| 5,756,111 A * | 5/1998 | Yoshikawa et al. | 424/402 |
| 6,989,035 B2 * | 1/2006 | Scheper et al. | 8/127.1 |
| 7,008,457 B2 * | 3/2006 | Sivik et al. | 8/115.6 |
| 7,125,967 B2 * | 10/2006 | Hung et al. | 536/20 |
| 7,144,431 B2 * | 12/2006 | Gardner et al. | 8/115.6 |
| 7,195,675 B2 * | 3/2007 | Okazaki et al. | 127/29 |
| 7,494,663 B2 * | 2/2009 | Kordes et al. | 424/405 |
| 8,092,732 B2 * | 1/2012 | Chou et al. | 264/207 |
| 8,152,893 B2 * | 4/2012 | Lin et al. | 75/347 |
| 8,193,325 B2 * | 6/2012 | Chou et al. | 536/20 |
| 8,318,913 B2 * | 11/2012 | Bristow | 536/20 |
| 8,420,005 B2 * | 4/2013 | Chou et al. | 264/555 |

(Continued)

FOREIGN PATENT DOCUMENTS

JP 08-092820 4/1996

*Primary Examiner* — Bobby Muromoto, Jr.
(74) *Attorney, Agent, or Firm* — Ming Chow; Sinorica, LLC

(57) ABSTRACT

An anti-"Methicillin-Resistant *Staphylococcus Aureus* (MRSA)" chitosan containing antibacterial High Wet Modulus (HWM) rayon fiber textile for medical usage is made of the steps as following: chitin flakes made from natural shrimp or crab shells are deacetylated to generate chitosan with a high deacetylation degree of 90% or more. Next chitosan is dissolved in acetic acid and regenerated by caustic soda to form a chitosan antibacterial nanoparticles slurry, then added to HWM viscose rayon process, and spinning to produce a chitosan containing antibacterial HWM rayon fiber. The antibacterial amino groups of chitosan and the hydroxyl groups of rayon cellulose combine together via hydrogen bonding. Therefore, the fiber becomes the anti-MRSA antibacterial HWM rayon fiber containing amino groups (—NH3+). Finally the resulting HWM rayon fiber is conducted via a yarn spinning or/and weaving process to procure a medical textile with chitosan content.

2 Claims, 2 Drawing Sheets

(56) References Cited

U.S. PATENT DOCUMENTS

| | | | |
|---|---|---|---|
| 8,496,956 B2* | 7/2013 | Chiu et al. | 424/426 |
| 2002/0115968 A1* | 8/2002 | Lin | 604/360 |
| 2003/0088923 A1* | 5/2003 | Sivik et al. | 8/115.51 |
| 2003/0106162 A1* | 6/2003 | Scheper et al. | 8/115.51 |
| 2003/0110573 A1* | 6/2003 | Gardner et al. | 8/115.51 |
| 2004/0176477 A1* | 9/2004 | Davison et al. | 516/77 |
| 2004/0254419 A1* | 12/2004 | Wang et al. | 600/8 |
| 2005/0025797 A1* | 2/2005 | Wang et al. | 424/422 |
| 2005/0079132 A1* | 4/2005 | Wang et al. | 424/1.11 |
| 2005/0092451 A1* | 5/2005 | Choi et al. | 162/146 |
| 2005/0107870 A1* | 5/2005 | Wang et al. | 623/1.44 |
| 2005/0236328 A1* | 10/2005 | Okazaki et al. | 210/634 |
| 2006/0052442 A1* | 3/2006 | Kordes et al. | 514/512 |
| 2007/0010702 A1* | 1/2007 | Wang et al. | 600/8 |
| 2007/0066627 A1* | 3/2007 | Hofmann et al. | 514/255.06 |
| 2007/0112183 A1* | 5/2007 | Kitano et al. | 536/20 |
| 2008/0064730 A1* | 3/2008 | Hofmann et al. | 514/357 |
| 2008/0241229 A1* | 10/2008 | Li et al. | 424/445 |
| 2009/0166916 A1* | 7/2009 | Chou et al. | 264/207 |
| 2009/0227784 A1* | 9/2009 | Chou et al. | 536/126 |
| 2009/0275745 A1* | 11/2009 | Bristow | 536/127 |
| 2010/0068240 A1* | 3/2010 | Chiu et al. | 424/423 |
| 2010/0133462 A1* | 6/2010 | Lin et al. | 252/62.54 |
| 2010/0204289 A1* | 8/2010 | Lodha et al. | 514/372 |
| 2010/0210745 A1* | 8/2010 | McDaniel et al. | 521/55 |
| 2010/0233146 A1* | 9/2010 | McDaniel | 424/94.2 |
| 2010/0297408 A1* | 11/2010 | Redlinger et al. | 428/206 |
| 2011/0008402 A1* | 1/2011 | Madhyastha et al. | 424/405 |
| 2011/0156299 A1* | 6/2011 | Chou et al. | 264/103 |
| 2011/0159546 A1* | 6/2011 | Carvalho Fernandes De Miranda Reis et al. | 435/85 |
| 2011/0240064 A1* | 10/2011 | Wales et al. | 134/26 |
| 2011/0250626 A1* | 10/2011 | Williams et al. | 435/18 |
| 2012/0097194 A1* | 4/2012 | McDaniel et al. | 134/26 |
| 2012/0154082 A1* | 6/2012 | Lin et al. | 335/296 |
| 2012/0183491 A1* | 7/2012 | Inoue et al. | 424/76.8 |
| 2012/0252755 A1* | 10/2012 | Henco et al. | 514/55 |
| 2012/0258089 A1* | 10/2012 | Madhyastha et al. | 424/94.61 |
| 2013/0108676 A1* | 5/2013 | Redlinger et al. | 424/401 |
| 2013/0122601 A1* | 5/2013 | Zhou et al. | 436/94 |
| 2013/0131563 A1* | 5/2013 | Ettner et al. | 601/148 |

* cited by examiner

MANUFACTURING METHOD OF MEDICAL TEXTILES WOVEN FROM CHITOSAN CONTAINING HIGH WET MODULUS RAYON FIBRE

FIELD OF THE INVENTION

The present invention relates to a manufacturing method of special high wet modulus rayon fibre containing chitosan. Nanoparticle grade chitosan slurry with high deacetylation degree (hereafter abbreviated as DAC) is uniformly mixed with viscose obtained from the posterior high wet modulus rayon fibre (hereafter abbreviated as HWM rayon fibre) process, then spun in the spin bath. The finishing cellulose is regenerated as an antibacterial chitosan containing HWM rayon fibre. Specifically to be notified, the antibacterial functional groups of the chitosan and the hydroxyl groups of the rayon cellulose are bonded to generate hydrogen bonds. Thus, the nanoparticles of chitosan are uniformly distributed on the skin and the core of fibres. As a result, the HWM rayon fibre has excellent antibacterial effect. The antibacterial activity will be more stable and long lasting. This fiber is less detracted by washing and friction. Importantly, it exhibits a high antibacterial effect to the Methicillin-Resistant *Staphylococcus Aureus* (hereafter abbreviated as MRSA) and thereby a steady long-term antibacterial textile for medical uses can be achieved.

BACKGROUND OF THE INVENTION

Over the past decade, the MRSA infection has gradually spread and infection rate has rapidly increased in hospitals and nursing homes, where patients with open wounds, invasive devices, and weakened immune systems are at greater risk of infection than the general public. The Methicillin-Resistant *Staphylococcus Aureus* base camp turns out to be hospitals around the world.

As shown by the monitoring data in Europe, the United States and Asian countries, the infection prevalence in Nordic countries and the Netherlands is below 5%, that in the United States is up to an average of 52%, in Asia's Taiwan, Japan, South Korea and China, the prevalence is over 50%. These show that MRSA and other medicine resistant bacteria are the prime culprit of today's nosocomial infections in the world.

Owning to the spread of MRSA in the hospitals, not only patients are threatened, but also huge losses for hospitals, communities and the country are caused. About 2 million people nosocomial infections in the United States each year cause 100,000 deaths, and cost $40 billion, equivalent to the total number of deaths and to total expenditures caused from breast cancer, AIDS and traffic accidents. Every year, around 3 million people in the EU catch a healthcare-associated infection, resulting in approximately 50,000 deaths.

Various countermeasures or solutions to improve and clean the living environment have been proposed to prevent a variety of bacteria spreading in the medical institutions, wherein one of the countermeasures is the hospital medical textile products, such as: hospital ward coverlets, beddings and pillows, as well as uniforms of medical staffs, or clothings of chronic disease stricken or critically ill patients in long-term care units to be changed into the use of antibacterial textiles, to deal with the rampant terror of MRSA and other medicine resistant bacteria (also known as super bacteria).

As for antibacterial textile products, the textiles uniforms worn by the existing health care workers so far have been made of cotton fabrics, whose cleaning process includes the high-temperature washing and chlorine sterilization to achieve sterile conditions before reuse. In going around and inspecting wards, physicians and nurses can not protect against bacteria attached to the hospital garments, thus MRSA or other microbes contaminated in ward A will be spread into ward B, ward C, so that the garments become the vehicle of nosocomial infections. This abnormal migrating infection phenomenon causes care and attention of Europe ECDC, the U.S. CDC and other government disease control departments.

In order to overcome the threat of MRSA bacteria on hospital-acquired infections, and the serious impact on patient health, and to improve the maintenance of the hospital environmental protection, an appropriate antibacterial textile is the EU R&D project to overcome the bacteria migrating infection phenomenon, relatively the multi-aspect searches for anti-MRSA antibacterial textiles are also being carried out in U.S.

The manufacturing and application development technology of the regular rayon fibres (or viscose fibres or regenerated cellulose fibres) has been known for more than a century, the said rayon fibres are made from a natural cellulose (wood pulp, cotton linter, etc.) via alkalization, xanthation to become cellulose xanthate, and then dissolved in the sodium hydroxide solution to produce viscose, which is filtered, ripened and extruded through a spinneret into the spin bath which contain sulfuric acid and zinc sulfate, then to obtain rayon tow, and finally stretched, cut, aftertreatment processed and dried to become a rayon fibre.

This rayon fibre can be used alone or with cotton, polyester, wool, nylon or acrylic fibre and other fibres at different blending ratios according to the required purposes. Physical and chemical properties of the rayon fibre are similar to those of cotton, the said rayon fibre exhibits good water absorption, good dyeing ability and comfort touching characteristics, but the dry tenacity (2.4 to 2.8 g/d) is poor, especially in the wet tenacity is only 50~60% of the dry tenacity, thus the resulting clothes tend to be deformed after washing. To overcome the insufficient tenacity of the above-mentioned rayon fibre, the advanced technology to produce a high tenacity rayon (2.8~3.2 g/d) and even a HWM rayon (3.8~4.2 g/d) are developed, making the tenacity thereof comparable to that of cotton, the rayon fibre tenacity deficiencies shortcomings are greatly improved to expand the application scope of HWM rayon in high function and fashion clothing.

Chitosan is derived from the shells of natural shrimps and crabs, which is treated to be a polymer with two biological characteristics including the collagen in the tissues of higher animals and the fibre in the organization of higher plants, and having a good adaptability to animals and plants. Chitosan decomposes in vivo by the action of enzymes, shows a compatibility between cells in vivo, thus exhibits low antigenicity, a great adsorption capacity of serum protein and other blood components, it is a non-toxic, odorless, biocompatible and biodegradable natural polymer antibacterial agent, therefore chitosan is recognized as an environmentally friendly safety green product in the 21st century.

Textiles with antibacterial or perspiring wicking, UV resistance, insulation properties and other functions have been developed, promoted and applied one after another, wherein the antibacterial agent used for antibacterial textiles includes quaternary ammonium salt, silver ion, photocatalyst or organic halide and so on, although textiles with the use of these antibacterial substances show antibacterial effects, when they are used in personal clothing or accessories, more or less bring about the human skin allergies or irritations, and their discard after use also pollutes the environment at the risk of causing environmental problems.

U.S. Pat. No. 5,756,111 and Japanese Patent Application—HEI-SEI No. 8-92820 reveal "the chitosan fibre and method of making the structure thereof", the technical manufacturing steps includes natural shrimp and crab shells→chitin→alkalization→xanthation→chitosan viscose, namely, the said chitosan powder of low deacetylation having the particle size below 4 mm is alkalized and xanthated similar to a rayon process reaction, the resulted chitosan viscose is added to the raw viscose made from a rayon process, and then the chitosan-containing rayon fibre is made from a general rayon manufacturing process, its tenacity is 2.4~2.8 g/d, similar to that of the regular rayon fibre. Owing to the low DAC chitosan, it generally exhibits low antibacterial rate against *Staphylococcus aureus* (53% antibacterial rate), thus this low DAC chitosan can be used only in the sanitary of the general personal clothings.

The general clothing of health care workers have been made from chitosan with DAC 70 to 85%, which is dissolved in an organic acid, and post-treated on the surface of a fabric; or 70 to 85% DAC chitosan is mechanically grounded into 100 mesh or finer particles, and added to a synthetic resin to become an adhesive, which is thoroughly mixed and used as the post-processing coating for the fabric. While such post-processing coating for the fabric surface has a little antibacterial effect, its antibacterial effect disappears shortly or decays after several washings, and the chitosan antibacterial agent coated fabric easily loses the original fabric physical properties such as softness and luster.

In view of the above, after several trial and error, research and investigation, the present inventor finds that firstly, DAC of chitosan is increased to more than 90%, then the resulted deacetylated chitosan is dissolved in acetic acid and regenerated by caustic soda to nanoparticle grade chitosan and become a chitosan antibacterial agent slurry having an average particle size of 100~600 nm, added to HWM rayon viscose with mixing, a chitosan containing HWM rayon fibre having a tenacity of 3.8~4.2 g/d is produced via a HWM rayon manufacturing process to improve the insufficient tenacity defect of the regular rayon fibre, meanwhile nanoparticle chitosan antibacterial functional groups and HWM viscose cellulose hydroxyl groups are combined to form hydrogen bonds, the resulting fully integrated chitosan antibacterial HWM rayon fibre is spun, woven to be able to overcome MRSA growth and migrating infection phenomena, which is quite different from the process and the function revealed in U.S. Pat. No. 5,766,111, therefore the present invention is completed.

SUMMARY OF THE INVENTION

In accordance with the present invention, the purpose of the present invention is to provide an efficient HWM rayon fibre which can inhibit MRSA growth and survival and have a long-lasting antibacterial function, and has no reduced textile tenacity, deformity, injury, etc. due to washing, can also be used in medical textiles to replace the natural cotton fabric used in the current medical care to improve the problem of MRSA nosocomial infections.

For achieving the purpose of the above-mentioned present invention, the present invention aims at the highly deacetylated nanoparticles (average particle size of 100~600 nm) chitosan antibacterial agent which is added and uniformly mixed in a ripened high alkalinity high degree of polymerization (hereafter abbreviated as DP) viscose obtained from the HWM rayon process, then contacted with a spin bath having low acidity at low temperature to regenerate cellulose, and spun to produce a chitosan antibacterial HWM rayon fibre. Because the chitosan antibacterial amino groups ($—NH_2$) and the regenerated cellulose hydroxyl groups ($—OH$) are bonded to generate hydrogen bonds to become the positively charged amino groups ($—NH_3^+$) of HWM antibacterial rayon fibre, so the resulted chitosan antibacterial HWM rayon fibre can be spun and woven via ordinary procedures to gain anti-MRSA textiles used in the field of medical applications. Not only the above-mentioned genuine chitosan antibacterial HWM rayon but also the blending with other natural fibres or synthetic fibres at different ratios of mixing can be woven into fabrics, wherein knitting, weaving, non-wovening can be used, interlock weaving and other means can be utilized to incorporate a variety of other fibres, thus anti-MRSA textiles to meet the medical requirements are achieved. The premise is that the net chitosan content in the final textile products should be maintained at more than 0.4 wt % to reach a more efficient anti-MRSA effect.

The chitosan antibacterial HWM rayon fibre produced in the present invention shows a net chitosan content above 0.4% by weight to endow an anti-MRSA antibacterial effect for medical textile products, not only can be applied against *Staphylococcus aureus* and *Escherichia coli*-positive Gram bacteria or negative Gram bacteria, but also can be widely used in antibacterial underwears, towels, bed sheets, blankets, masks, gloves or socks, and other hygiene items, and personal clothing and other purposes.

The present invention concerns a high antibacterial chitosan containing HWM rayon textile product used in the medical field to prevent MRSA infection in the hospital, and the present inventive textile product contains chitosan nanoparticles with more than 90% of high DAC and average particle size of 100~600 nm, which fully binds with rayon fibre through hydrogen bonding, therefore the resulted long-lasting antibacterial textiles still exhibit a very high anti-MRSA antibacterial effect after washing more than 30 times in the general washing conditions at room temperature.

To make the present invention more clear, the semantics of the raw materials used in the specification will be explained in detail as follows:

1) Chitosan differs from chitin in that it has free amino groups and is obtained by deacetylation chitin. At a minimum deacetylation level of 70% (=amount of free amino groups in the polymer) it is considered to be chitosan, a beta-1,4-glucosamine linear amino($NH_2$) natural polymer having the molecular formula $[C_6H_{11}NO_4]_n$ and the structure formula:

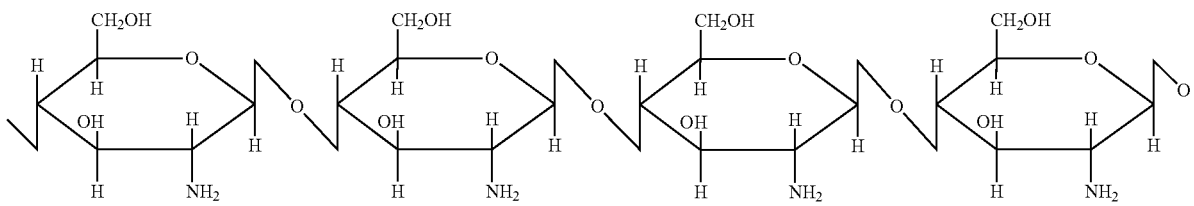

2) Degree of deacetylation, abbreviated as DAC.

During the deacetylation process, chitin undergoes a treatment with lye to divide the acetyl groups from the polymer, resulting in chitosan. This has a variation of properties depending on the degree of deacetylation and chain length; in general, food-grade products should have DAC above 80%. Natural shrimp and crab shells after decalcification and deprotein show the ratio of chitosan/chitin is about 10/90, after deacetylation its ratio may be raised to 90/10 (i.e. DAC 90%).

3) Rayon fibre is made from the alkalization of natural wood pulp with NaOH, which is xanthated with $CS_2$ to cellulose xanthate, then dissolved in a NaOH solution into viscose, ripened after a multi-stage filtration, then extruded through a Pt/Au spinneret, and reacted with sulfuric acid in the spin bath, and then drawn so that cellulose is regenerated to become rayon tow, and finally cut into fibre chip and aftertreatment (fleeceformed, desulfurized, bleached, washed, oiling), and dried to acquire a rayon fibre.

4) High Wet Modulus rayon fibre (abbreviated as HWM rayon fibre) is made from the alkalization of a high polymerization degree (DP) and high α-cellulose wood pulp with NaOH, then xanthated with $CS_2$ to cellulose xanthate, and dissolved in a NaOH solution to become high DP viscose, ripened via a multi-stage filtration, then extruded through a Pt/Au spinneret and contacted with a spin bath having a low sulfuric acid ($H_2SO_4$) concentration at low temperature, and then highly stretched to regenerate cellulose into HWM rayon tow, and finally tow cut into fibre chip and aftertreatment (fleeceformed, desulfurized, bleached, washed, oiling), dried to acquire a HWM rayon fibre. Its molecular formula is $[C_6H_{10}O_5]_n$ with the structural formula:

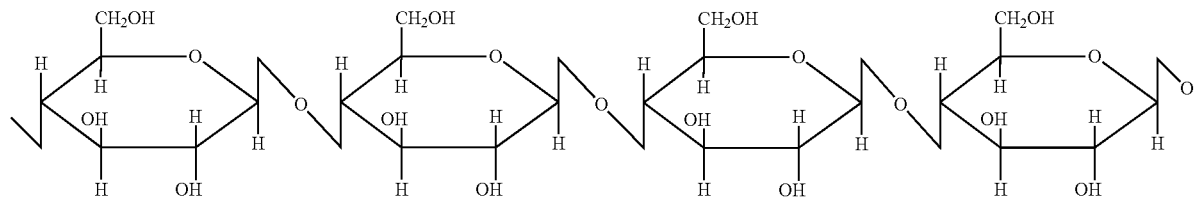

5) *Staphylococcus aureus* is a bacterial species named from Greek σταφυλόκοκκος meaning the "golden grape-cluster berry". Also known as "golden staph" and Oro staphira, it is a facultative anaerobic Gram-positive coccal bacterium. It is frequently found as part of the normal skin flora on the skin and nasal passages. It is estimated that 20% of the human population are long-term carriers of *S. aureus*. *S. aureus* can cause a range of illnesses, from minor skin infections to life-threatening diseases. It is still one of the five most common causes of nosocomial infections and is often the cause of postsurgical wound infections. Each year, some 500,000 patients in American hospitals contract a staphylococcal infection.

6) Methicillin-resistant *Staphylococcus Aureus* (MRSA) is a bacterium responsible for several difficult-to-treat infections in humans. MRSA is any strain of *Staphylococcus aureus* that has developed resistance to beta-lactam antibiotics, which include the penicillins (methicillin, dicloxacillin, nafcillin, oxacillin, etc.) and the cephalosporins. The development of such resistance does not cause the organism to be more intrinsically virulent than strains of *Staphylococcus aureus* that have no antibiotic resistance, but resistance does make MRSA infection more difficult to treat with standard types of antibiotics and thus more dangerous. MRSA is especially troublesome in hospitals and nursing homes, where patients with open wounds, invasive devices, and weakened immune systems are at greater risk of infection than the general public.

7) Chitosan antibacterial HWM rayon is made from chitin of natural shrimp or crab shells, said chitin is impregnated in high concentration NaOH at high temperature to be deacetylated to get chitosan of more than 90% DAC, then the resulted deacetylated chitosan is dissolved in acetic acid and regenerated by caustic soda to nanoparticle grade chitosan and become a chitosan antibacterial agent slurry having an average particle size of 100~600 nm, evenly added and mixed in high alkalinity and high DP viscose which has been ripened from a HWM rayon fibre process, then extruded through a Pt/Au spinneret to contact with the spin bath having low sulfuric acid concentration at low temperature, and highly stretched to regenerate cellulose, thereby resulted in an antibacterial chitosan HWM rayon fibre, wherein the functional amino groups of chitosan nanoparticles and the hydroxyl groups of rayon cellulose are bonded to produce hydrogen bonds as the following combination structure, which allows chitosan to be uniformly distributed on skin and in core of the HWM rayon fibre, therefore chitosan will not lose the bacterial inhibitory function due to friction or washing.

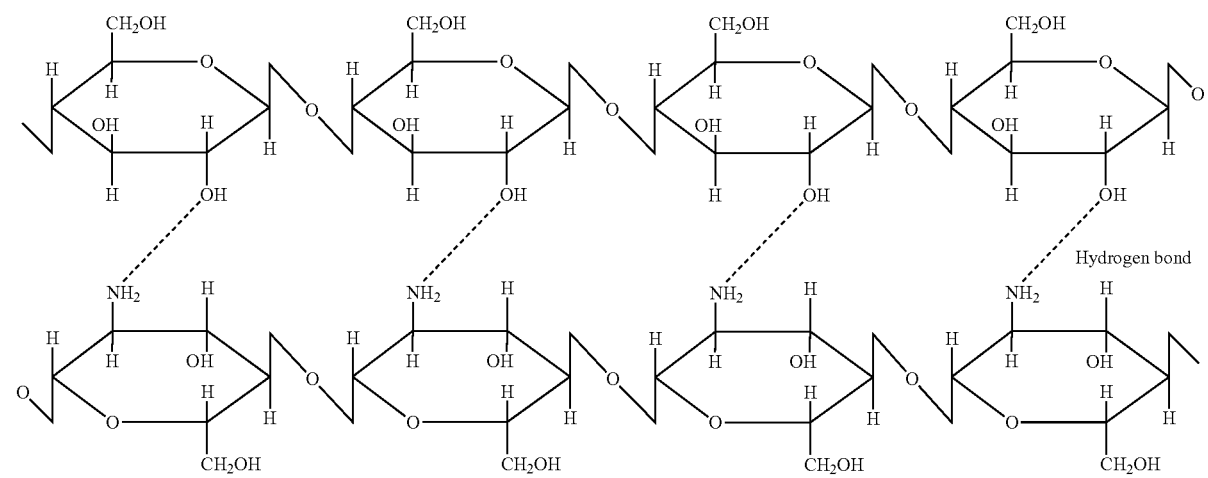

DETAILED DESCRIPTION OF THE PREFERRED EMBODIMENT

Figure 1:
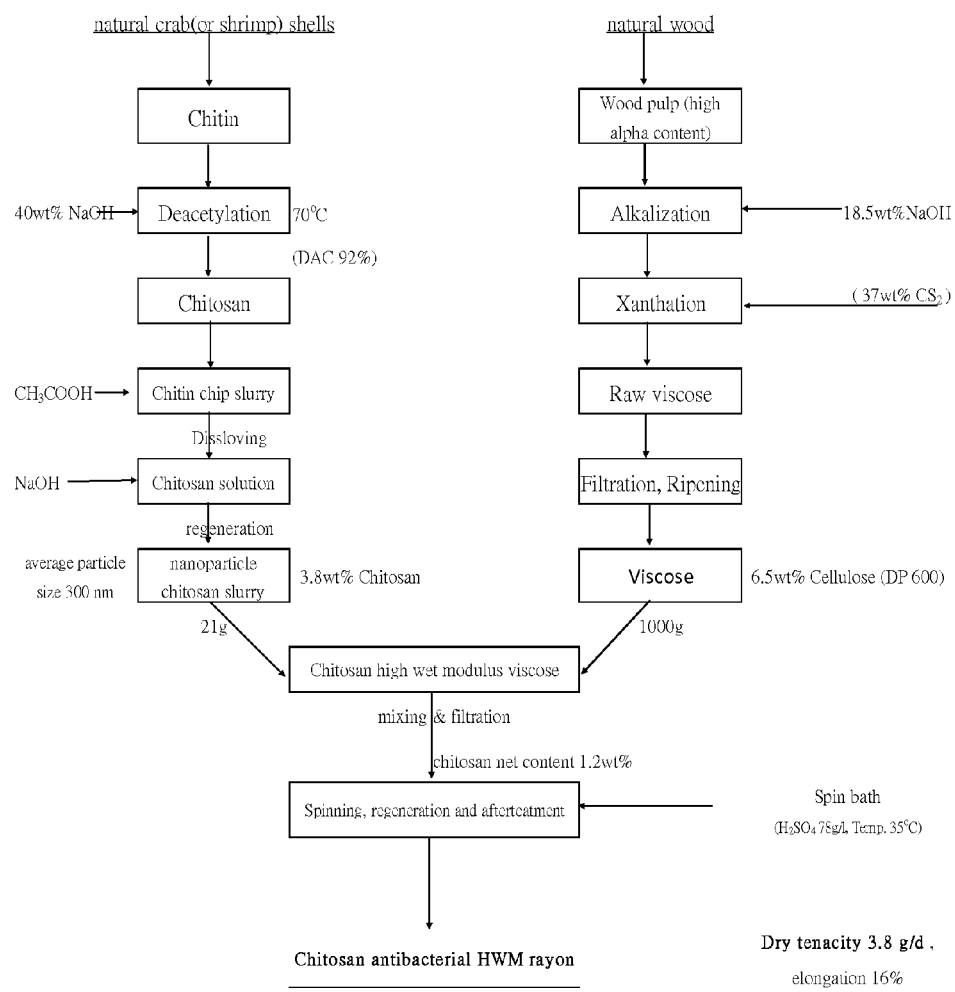
FIG. 1 is a production flow diagram of the present inventive chitosan antibacterial HWM rayon fibre.
Figure 2:
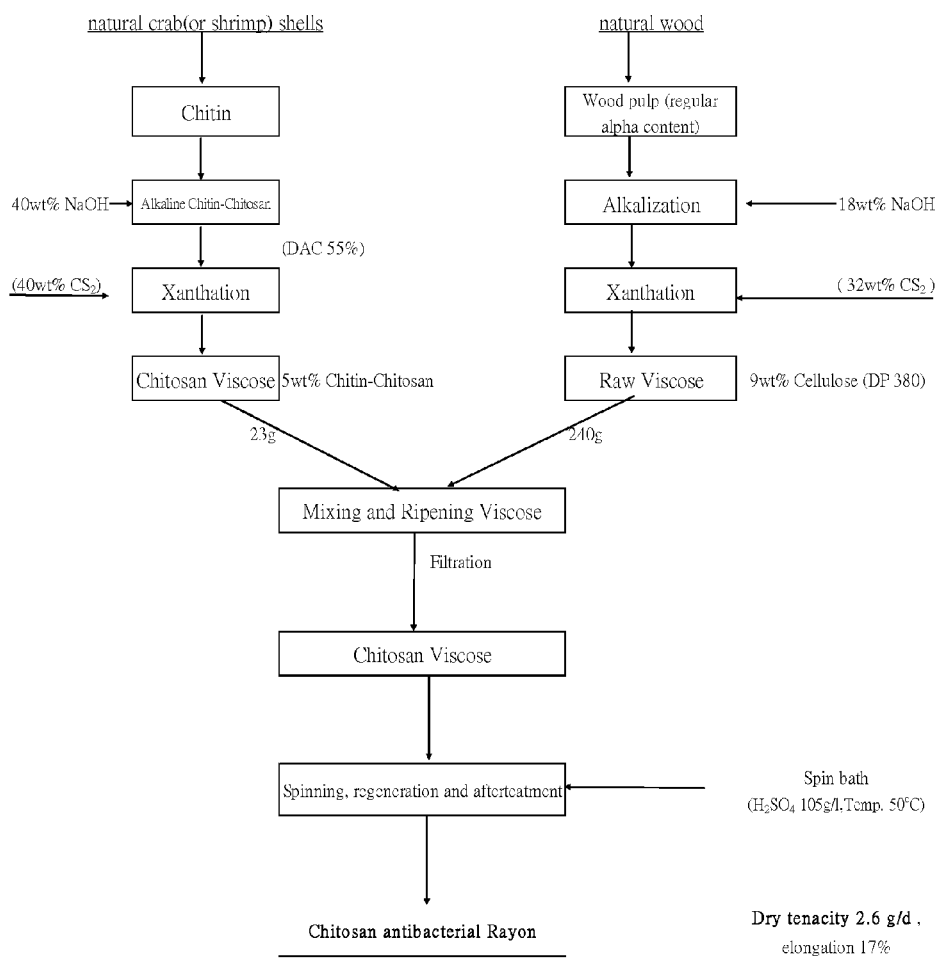
FIG. 2 is a process flow diagram of the chitosan antibacterial rayon fibre disclosed in U.S. Pat. No. 5,758,111.

The present inventive anti-MRSA chitosan containing HWM rayon fibre textile used in the field of medical care is improved from a known HWM rayon fibre in the existing technology, characterized in that a high DAC chitosan antibacterial agent is nanominiaturized to an average particle size of 100~600 nm, and more than 90% thereof is deacetylated, then evenly added and mixed in high alkalinity and high DP viscose which has been ripened in a HWM rayon fibre process, again contacted with a spin bath having low acidity at low temperature to regenerate cellulose, which is then spun into a chitosan antibacterial HWM rayon fibre; again turned into anti-MRSA medical used antibacterial textiles via a general spinning and weaving process, the resulted antibacterial textiles maintain more than 0.4 wt % of the net chitosan content. The aforementioned anti-MRSA chitosan containing HWM rayon fibre in the form of 0.3 to 5.0 wt % nanoparticles chitosan anti-bacterial agent is evenly mixed with HWM rayon viscose, after filtrated and extruded through a spinneret, then contacted with a spin bath having proper low concentration sulfuric acid of 70 to 100 g/L at low temperature conditions of 35~45° C. to conduct the regeneration reaction of cellulose to procure chitosan antibacterial HWM rayon fibre tow, and then by stretching, cutting fibre into fleeceformer, then desulfurizing, bleaching, water washing, oiling, finally drying to become an anti-MRSA chitosan containing HWM rayon fibre.

In the present invention, nanominiaturized chitosan dispersed on the fibre skin and core the fibre is strongly closely bonded with rayon cellulose via hydrogen bonds; the outer electrons of the nano-chitosan functional groups—amino groups are not saturated, thus easy to capture hydrogen ions ($H^+$) to form stable positively charged amino groups ($—NH_3^+$). The positively charged amino group ($—NH_3^+$) can be easily attached to the bacteria on the fibre surface or within pore, such as Gram-positive bacteria or Gram-negative bacteria etc. to let the bacterial surface generate electrification, thus cut off its DNA replication to propagate the next generation by the uneven charge distribution, and further realize the antibacterial effect.

The raw material of the above-mentioned chitosan used in the present invention is derived from natural shrimp or crab shells, which are treated with a dilute acid and caustic soda (NaOH) to remove calcium, protein, lipid and colorant and other impurities, resulted in chitin. If the DAC of chitin below about 10%, most of the antibacterial functional groups ($—NH_2$) are still covered by acetyl groups, then the antibacterial effect is insufficient, thus 1 or 2 times of deacetylation reaction should be necessary to significantly enhance the deacetylation degree up to 90% or more before they can exhibit a higher antibacterial function. Chitosan used in this invention has deacetylation degree of 90% or more, then through the molecular weight adjusting, microcrystalline nanominiaturization, and purification, resulted in a nano microcrystalline chitosan antibacterial agent to highlight its antibacterial effect.

Another so-called HWM rayon is made from 99% alpha-cellulose containing wood pulp obtained from natural wood, then pulp is alkalized with sodium hydroxide to give alkalized cellulose, after aged, $CS_2$ xanthated to become cellulose xanthate, then added in a sodium hydroxide solution to dissolve into viscose, and then by multi-filtrations to remove undissolved fibre and impurities, HWM ripened viscose is produced.

The above obtained anti-MRSA chitosan HWM rayon fibre shows that the fibre denier can be controlled at 1.0 to 1.5 denier, may also meet the actual needs to spin more than 2.0 denier, possessing a dry tenacity of 4.0±0.2 g/d, a wet tenacity of 2.6±0.2 g/d and maintaining a long-lasting natural antibacterial effect, exhibiting better soft comfortable touching and higher water absorption capacity than those of cotton, resulting in an excellent skin affinity, biodegradable and environmentally friendly anti-bacterial fibre.

The present inventive chitosan antibacterial HWM rayon fibre can also be blended in whole or in part with cotton, polyester at different mixing ratios, and spun into a 10's~50's yarn via a general known yarn spinning technology to match the needs of different applications. The chitosan antibacterial HWM rayon fibre can also be twisted into a two-thread yarn; or blend-spun in warp or weft, then interwoven with other kinds of yarn through a weaving process including knitting machines or shuttle looms to weave into an anti-MRSA anti-bacterial textile applied in the medical care field.

Therefore, the present inventive yarn can be a pure chitosan antibacterial HWM rayon fibre, can also be a blended yarn with other natural fibres or synthetic fibres at a different ratio, and woven via knitting machines, or shuttle looms or water jet looms or air jet looms and other different weavings, the process can also be in coordination with the other functional and epidemic needs to use interweaving and yarn covering means for incorporation of a variety of different fibre components, if a higher anti-MRSA effect is required, the net chitosan content in the ultimate textile products should be maintained at more than 0.4% by weight.

The main applications of the present inventive anti-MRSA chitosan HWM rayon textiles are uniforms or coveralls of physicians and nurses in medical institutions, community cares or home cares; and isolation gowns, bed sheets, quilt related bedding and bath towel used in wards and clinics etc., and wiping cloths and gauzes, bandages, masks, stickers and other textile products for medical related uses. As a result, you can improve and purify the living environment, and prevent the spreading migrating infection phenomena of MRSA and other bacteria in medical institutions or community homes.

EXAMPLES

The present invention will be described in detail below with reference to best embodiments for purposes of exemplification and illustration only, but the inventive claims are not subject to the limitations of the embodiments, the antibacterial test is carried out in accordance with JIS L 1902:2008 standard, the used strains are Methicillin-Resistant *Staphylococcus aureus* ATCC 33591, *Staphylococcus aureus* ATCC 65389.

Example 1

Chitin flakes having a particle diameter of 10 mm obtained from natural shrimp and crab shells are impregnated in 40 wt % NaOH solution at temperature of 70° C. to be deacetylated to generate chitosan having DAC 92%, then dissolved in 1 to 10 wt % acetate and regenerated from 1 to 5 wt % caustic soda, resulted in an antibacterial agent slurry containing 3.8 wt % (solids basis) chitosan with an average particle size of 300 nm.

The nanoparticles of a chitosan antibacterial agent 21 g (chitosan solid accounted for 0.8 g) having an average particle size of 300 nm are added to 1000 g HWM rayon viscose made of an existing technology (cellulose solid accounted for 65 g), thoroughly mixed and filtrated, then fed with pressure through a Pt/Au spinneret to a spin bath, thereafter spun, regenerated, aftertreatment and dried, thus a chitosan antibacterial HWM rayon fibre with a net chitosan content 1.2 wt % {0.8/(0.8+65)=1.2%} is obtained.

The fibre properties of the chitosan antibacterial HWM rayon fibre are determined as follows:

fibre dry tenacity: 3.8 g/d, dry elongation:16%,
fibre wet tenacity: 2.4 g/d, wet elongation:18%,
antibacterial value of anti-"*Staphylococcus aureus*": 6.20 (antibacterial rate: 99.9%↑) higher than the JIS standard value of 2.0. antibacterial value of anti-"Methicillin-Resistant *Staphylococcus Aureus*": 5.79 (antibacterial rate of 99.9%↑), the anti-MRSA effect is very good.

Comparative Example

U.S. Pat. No. 5,756,111 titled "Process for producing articles of regenerated chitin-chitosan containing material and the resulting articles" discloses the technical steps including natural shrimp and crab shells→chitin→alkalization→xanthation→chitosan viscose, in other words, a low-deacetylated chitin powder having diameter under 4 mm is alkalized and xanthated similar to a rayon manufacturing process to get chitosan viscose, which is different from the present application, then it is added to raw viscose made from a rayon process, and thereafter resulted in a chitosan containing rayon fibre via a regular rayon manufacturing process, its fibre tenacity is equal to 2.4~2.8 g/d similar to that of a regular rayon fibre. Because chitosan with a low DAC shows a lower antibacterial (antibacterial rate 53%) effect to a general *Staphylococcus aureus*, it cans only used in general personal sanitary clothing.

Example 2

The chitosan antibacterial HWM rayon fibre obtained in Example 1 is spun into an antibacterial 36$^{ts}$ yarn, then woven, dyed and finished into specifications of 80"×260 g/yard (wherein the net chitosan content is 1.2 wt %). The antibacterial properties are measured after washing 30 times;

The antibacterial value of anti-"*Staphylococcus aureus*" is 3.50 (antibacterial rate of 99.9%↑), Antibacterial value of anti-"Methicillin-Resistant *Staphylococcus aureus*" is 2.86 (antibacterial rate of 99%↑), the effect of anti-MRSA is good.

Example 3

The chitosan antibacterial HWM rayon fibre obtained from Example 1 is blended with cotton at a blend ratio of 50% to 50%, then spun via a yarn spinning process into a 40$^{ts}$ yarn, wherein the net chitosan content accounts for 0.6 wt % {1.2*0.5=0.6%}, then interwoven with polyester filaments at 2 to 1 ratio into a interwoven fabric having a net chitosan content of 0.4 wt % {0.6*2/3=0.4%}, finally via a dyeing process, resulted in an antibacterial interwoven fabric with specifications of 61"×240 g/yard.

The antibacterial properties are measured after washing 20 times;

The antibacterial value of anti-"*Staphylococcus aureus*" is 5.42 (antibacterial rate of 99.9%↑)

The antibacterial value of anti-"Methicillin-Resistant *Staphylococcus aureus*" is 6.05 (antibacterial rate of 99.9%↑), The anti-MRSA effect is good.

The invention claimed is:

1. A process to produce a medical textile woven from a chitosan containing HWM (High Wet Modulus) rayon fibre, characterized by the steps as follow:
   (1) impregnating chitin flakes obtained from natural shrimp or crab shells with 30~48% by weight of NaOH solution at temperature of 40~95° C.;
   (2) generating a chitosan with a deacetylation degree of more than 90% via a deacetylation processing;
   (3) dissolving said chitosan into 10% by weight of acetic acid;
   (4) generating a nanominiaturized chitosan with 1-5% by weight of caustic soda, wherein said nanominiaturized chitosan having an average particle size of 100-600 nm;
   (5) generating an antibacterial agent slurry with said nanominiaturized chitosan;
   (6) evenly mixing said antibacterial agent slurry with an HWM rayon viscose to obtain a first mixture, wherein said HWM rayon viscose is derived from wood pulp through a high alkalinity condition and with a high degree of polymerization;
   (7) contacting said first mixture with a spin bath under a low acidity and low temperature condition for neutralization;
   (8) combing amino groups of said nanominiaturized chitosan in said first mixture with hydroxyl groups of a rayon cellulose in said HWM rayon viscose via hydrogen bonds, wherein said amino groups are antibacterial functional groups;
   (9) generating an HWM antibacterial fibre containing positively charged amino groups ($—NH_3^+$);
   (10) making a yarn through a spinning process and/or weaving program; and
   (11) obtaining an anti-MRSA (Methicillin-Resistant *Staphylococcus aureus*) textile.

2. The process to produce a medical textile woven from a chitosan containing HWM rayon fibre according to claim 1, wherein a net chitosan content in the said anti-MRSA textile medical textile is more than 0.4% by weight.

* * * * *